(12) United States Patent
Asa

(10) Patent No.: US 6,194,199 B1
(45) Date of Patent: Feb. 27, 2001

(54) CELL SCRAPER DEVICE HAVING BLADE ON HANDLES WITH PIVOTAL JOINTS

(75) Inventor: David Asa, Carmel, CA (US)

(73) Assignee: Michael Hoffman, Carmel, CA (US)

( * ) Notice: Subject to any disclaimer, the term of this patent is extended or adjusted under 35 U.S.C. 154(b) by 0 days.

(21) Appl. No.: 09/396,298

(22) Filed: Sep. 15, 1999

Related U.S. Application Data

(60) Provisional application No. 60/100,756, filed on Sep. 17, 1998.

(51) Int. Cl.$^7$ ..................................................... C12M 1/26
(52) U.S. Cl. .................................... 435/309.1; 435/309.2; 15/236.01
(58) Field of Search ............................. 435/308.1, 309.1, 435/309.2; 15/104.05, 104.16, 104.18, 236.01

(56) References Cited

U.S. PATENT DOCUMENTS

| | | | |
|---|---|---|---|
| D. 350,603 | 9/1994 | Firlik | D24/119 |
| 4,010,077 | 3/1977 | Pardos | 195/127 |
| 4,687,746 | 8/1987 | Rosenberg et al. | 435/292 |
| 4,810,652 | * 3/1989 | Witt . | |
| 4,892,831 | 1/1990 | Wong | 435/292 |
| 5,462,063 | 10/1995 | Kist et al. | 128/756 |
| 5,900,374 | * 5/1999 | Otto-Nagels | 435/379 |

* cited by examiner

*Primary Examiner*—David A. Redding
(74) *Attorney, Agent, or Firm*—Flanagan & Flanagan; John K. Flanagan; John R. Flanagan

(57) ABSTRACT

A cell scraper device includes a pair of elongated handles, a blade and a pair of spaced apart pivotal joints. The handles enable a user to hold and to operate the device. Each handle has a pair of opposite ends and a longitudinal axis extending between the opposite ends. The handles are spaced apart from and disposed along one another and movable in opposite directions along their longitudinal axes. Each joint, such as a pivotal ball type or a living hinge type, pivotally joins the blade to one of a pair of adjacent ends of the handles such that the blade is pivotally movable between a closed position and an open position upon corresponding movement of the handles in the opposite directions along their longitudinal axes. The blade in the closed position is disposed at an acute angle relative to the longitudinal axis of each handle and on a side of the handle such that the blade and handles are positioned for insertion into and removal from a culture flask. The blade in the open position is disposed in a substantially transverse relationship to the longitudinal axes of the handles such that the blade provides a rake head that can be drawn past a culture medium on an interior surface of the culture flask so as to collect and bring layers of cells growing on the culture medium to an area adjacent to a top opening of the culture flask for decanting the layers of cells from the culture flask.

20 Claims, 2 Drawing Sheets

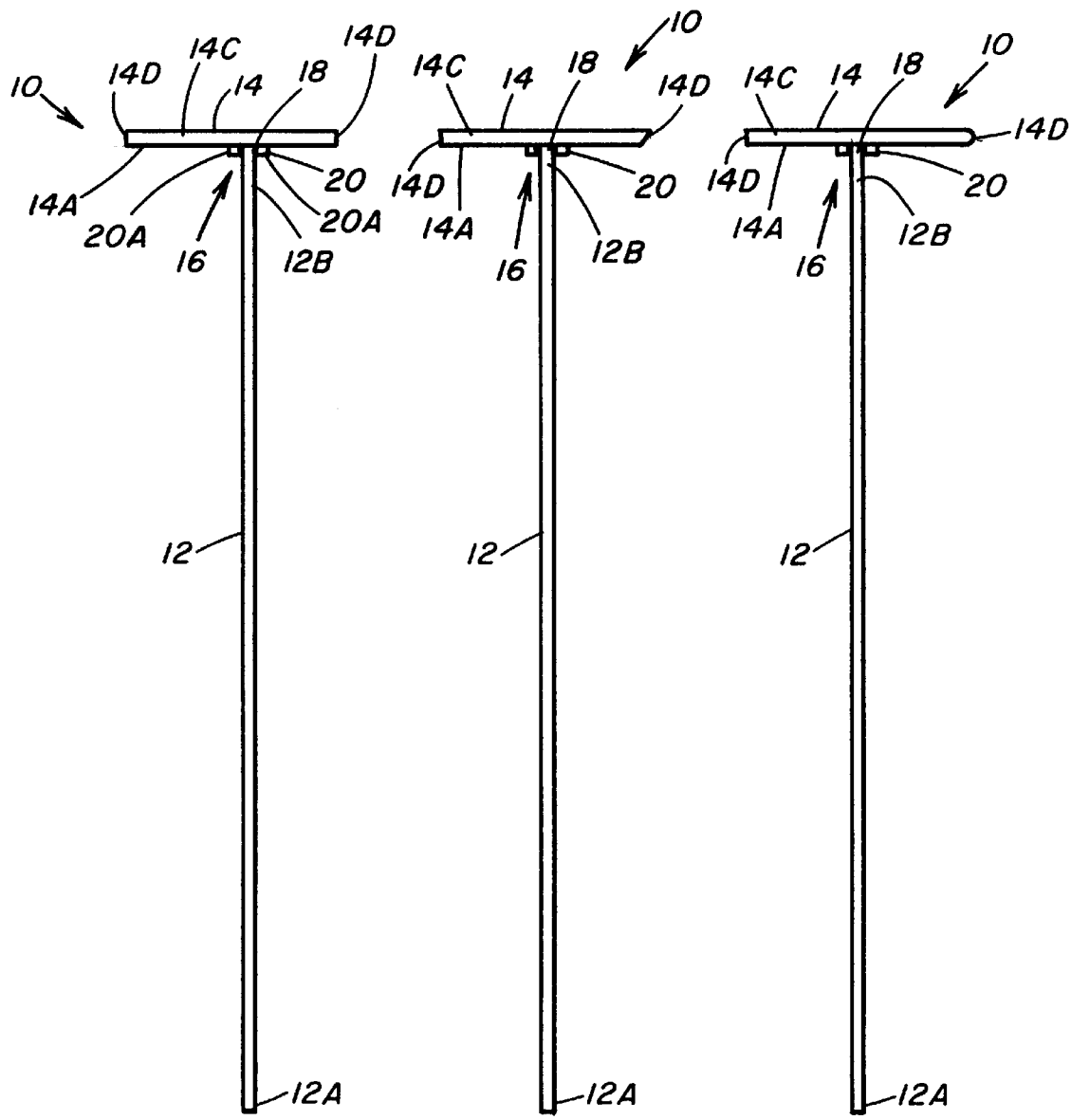
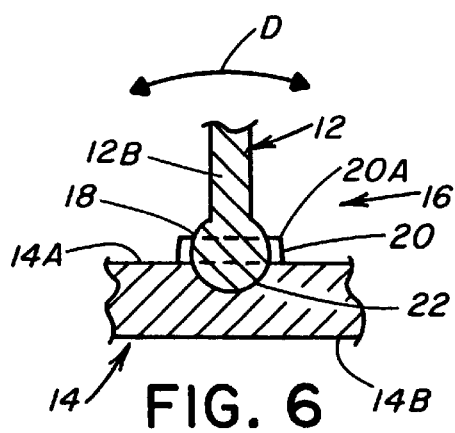
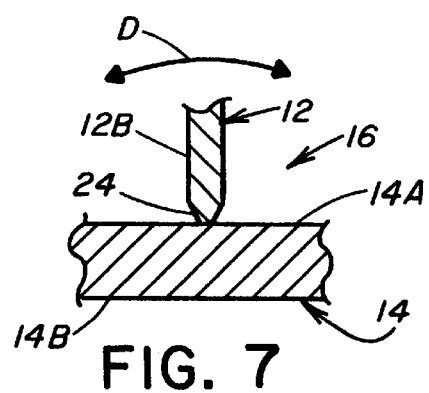
FIG. 3　　　FIG. 4　　　FIG. 5
FIG. 6　　　FIG. 7

CELL SCRAPER DEVICE HAVING BLADE ON HANDLES WITH PIVOTAL JOINTS

CROSS-REFERENCE TO RELATED PATENT APPLICATION

This patent application claims the benefit of U.S. provisional application No. 60/100,756, filed Sep. 17, 1998.

Reference is hereby made to a copending related U.S. patent application entitled "Cell Rake Device For Collecting Layers Of Cells Grown Inside Culture Flasks" by David Asa, assigned Ser. No. 09/346,461 and filed Jul. 1, 1999.

BACKGROUND OF THE INVENTION

1. Field of the Invention

The present invention generally relates to collection of cell colonies grown on culture media and, more particularly, is concerned with a cell scraper device having a blade on a pair of handles with pivotal joints connecting the blade to the handles.

2. Description of the Prior Art

Microorganisms are often grown by scientists and others on culture media in petri dishes, culture flasks or the like, for various reasons. Cell colonies grown on culture media are typically grown across a mono-layer of culture medium on a treated plastic surface. The surface is generally treated with a substrate which is usually a chemical coating attached to the plastic. The substrate allows for high densities of cells to grow over a given surface area.

After a predetermined period of time when maximum cell growth is achieved, the cells are ready to be harvested, which involves lifting and removing intact layers of cells from the culture medium. The cells are suspended in the culture medium when they are lifted from the surface of the dish or flask and are decanted into tubes or other containers for further use or analysis. Special care must be taken during this process so that the viability of the cells is maintained and a maximum level of cell recovery is achieved.

A variety of devices have been developed over the years for collecting cell colonies grown on culture media and/or for inoculating culture media with cell colonies. Representative examples of prior art cell colony collection and/or inoculation devices are disclosed in U.S. Pat. No. 4,010,077 to Pardos, U.S. Pat. No. 4,687,746 to Rosenberg et al., U.S. Pat. No. 4,892,831 to Wong, U.S. Pat. No. 5,462,063 to Kist et al. and U.S. Des. Pat. No. 350,603 to Firlik. The Pardos patent discloses a transfer device which includes a plurality of circumferentially spaced fingers extending generally in a common axial direction from a base and diverging from one another. The Rosenberg et al. patent discloses a transfer device which includes a tip at one end of a handle and a loop at the other end of the handle. The Wong patent discloses an inoculating device which includes a loop at one end of a handle and a picker with a pyramidal-shaped head at the other end of the handle. The Kist et al. patent discloses a cell collecting device which includes a handle and a brush head formed of flexible bristles. The bristles can be arranged such that central bristles are surrounded by outer bristles that are shorter and thinner than the central bristles. The bristles can also be arranged in a pattern of concentric circles. The Firlik patent discloses a cell culture scraper which includes a handle and a plate with serrations along an edge thereof at one end of the handle. The fingers of the Pardos device, the tip and loop of the Rosenberg et al. device, the loop and picker of the Wong device, the brush of the Kist et al. device and the plate with serrations of the Firlik device are all adapted to be used to collect a bacteriological specimen or to plate or streak cells on a growth medium. There are other prior art devices known as "cell lifters" or "cell scrapers" which are available to lift or scrape cells from surfaces and into culture media for decanting.

While these prior art cell colony collection and inoculation devices appear to be satisfactory in use for the specific purposes for which they were designed, none of them seem to provide an effective solution for collecting layers of cells which are grown on media inside culture flasks. The problem with these prior art devices is that they do not adequately or easily reach or access the entire interior surface of a tissue culture flask. In addition, their features can cause significant loss of viable cell populations due to damage to cell walls in the process of contacting and scraping the cells from wall surfaces.

Consequently, a need still exists for a device which provides a more effective solution to the aforementioned problems of the prior art devices without introducing any new problems in place thereof.

SUMMARY OF THE INVENTION

The present invention provides a cell scraper device designed to satisfy the aforementioned need. The cell scraper device of the present invention is particularly suited for collecting layers of cells grown inside culture flasks although the device is suitable for other applications as well. The cell scraper device provides adequate and easy access to the culture medium on the entire interior surface of the culture flask while minimizing loss of viable cell populations due to damage to cell walls which may otherwise occur in the process of contacting the cells.

Accordingly, the present invention is directed to a cell scraper device which comprises: (a) a pair of elongated handles for enabling a user to hold and to operate the device, each of the handles having a pair of opposite ends and defining a longitudinal axis extending between the opposite ends, the handles being spaced apart from and disposable along one another and movable in opposite directions along the longitudinal axes; (b) a blade; and (c) means for pivotally joining the blade to a pair of adjacent ones of the opposite ends of the handles such that the blade is pivotally movable between a closed position and an open position relative to the handles upon corresponding movement of the handles in the opposite directions along the longitudinal axes thereof. The blade in the closed position is disposed at an angle of a first size relative to the longitudinal axis of each of the handles along a side of the handles at the pair of adjacent ones of the ends thereof such that the blade and handles are positioned for insertion into and removal from a culture flask through a top opening thereof. The blade in the open position is disposed at another angle of a second size relative to the longitudinal axis of each of the handles which is larger than the angle of the first size such that the blade provides a rake head that can be drawn past a culture medium on an interior surface of the culture flask so as to collect and bring layers of cells growing on the culture medium to an area adjacent to the top opening of the culture flask for decanting the layers of cells from the culture flask.

More particularly, the handles of the device are substantially identical with each handle having a longitudinal length greater than a longitudinal length of the blade. Also, the blade has a substantially flat rectangular configuration and a bottom edge which may be flat, beveled or rounded. Furthermore, the blade is movable between a pair of opposite closed positions and the open position upon corresponding movement of the handles in the opposite directions along the longitudinal axes thereof. The blade in either of the opposite closed positions is disposed at substantially the same acute angles relative to the longitudinal axes of the handles and disposed on either side of the handles.

The means for pivotally joining the blade to the handles of the device preferably comprises a pair of spaced apart pivotal ball joints. Each pivotal ball joint includes a socket mounted to one of the blade and to one of the adjacent ends of pair thereof of the handles, and a ball mounted to the other of the blade and the one of the adjacent ends of the pair thereof of the handles. The balls of the pivotal ball joints are rotatably interfitted with the sockets of the pivotal ball joints such that the blade is pivotally mounted to the pair of adjacent ends of the handles and movable between either closed position and the open position upon the corresponding movement of the handles in the opposite directions along the longitudinal axes thereof. The pivotal joining means, alternatively, can be a pair of living hinge joints pivotally joining the blade to the pair of adjacent ones of the opposite ends of the handles.

These features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 3 is a front elevational view of the cell scraper device showing the blade with a flat scraping edge.

FIG. 4 is a view of the cell scraper device similar to that of FIG. 3 but showing the blade with a beveled scraping edge.

FIG. 5 is a view of the cell scraper device similar to that of FIGS. 3 and 4 but showing the blade with a rounded scraping edge.

FIG. 6 is an enlarged detailed sectional view of the portion of the device enclosed by circle 6 in FIG. 2 showing, in a preferred embodiment, one of a pair of ball joints pivotally joining the blade to the handles of the device.

FIG. 7 is a view similar to that of FIG. 6 but showing, in an alternative embodiment, one of a pair living hinge joints pivotally joining the blade to the handles of the device.

DETAILED DESCRIPTION OF THE INVENTION

Figures 1, 2:
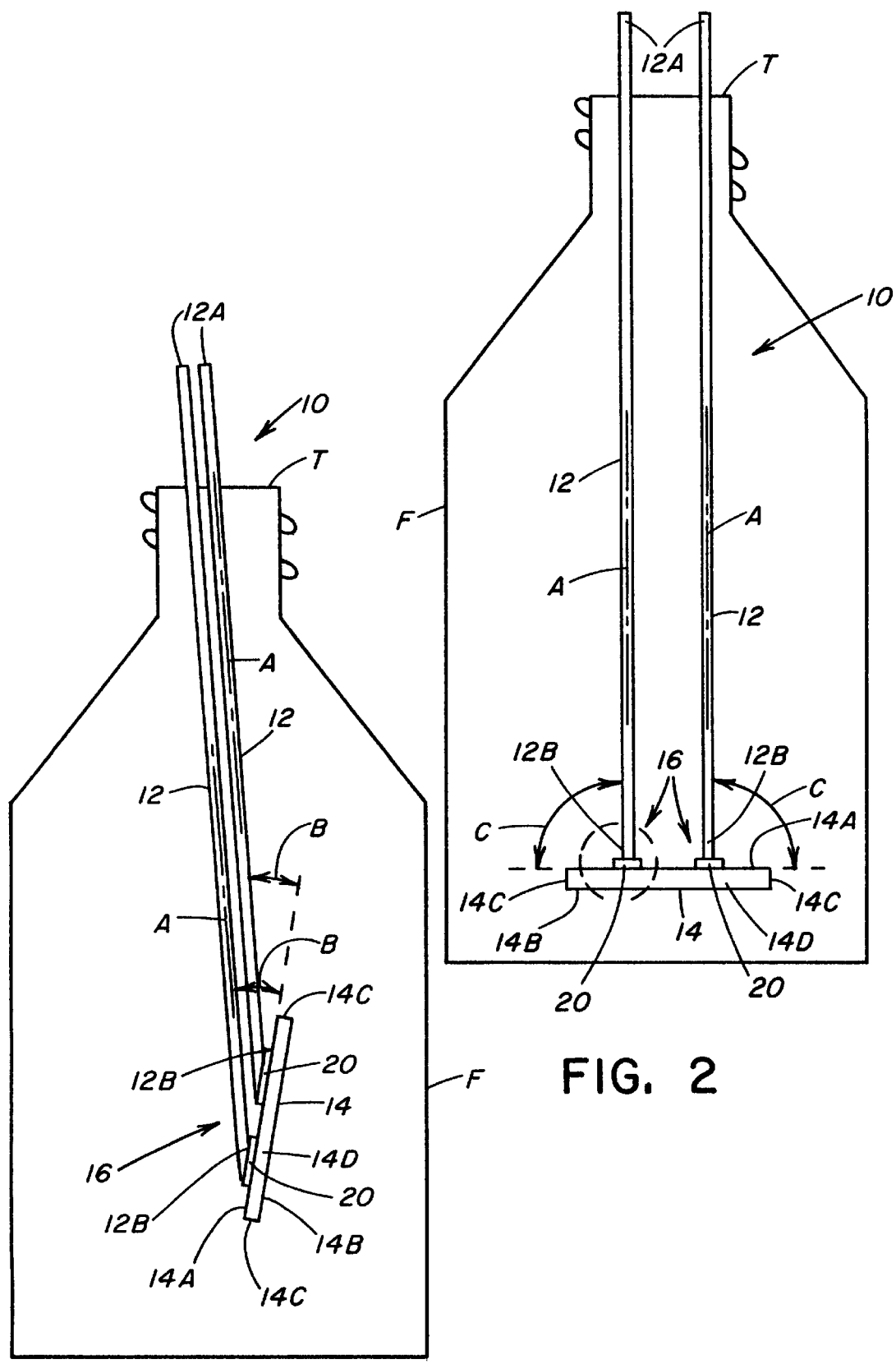
FIG. 1 is a side elevational view of a cell scraper device of the present invention showing a pair of elongated handles, a blade and a pair of pivotal joints pivotally joining the blade to the handles with the blade in a closed position relative to the handles for insertion into and removal from a culture flask and showing the device disposed within the culture flask.
FIG. 2 is a view of the cell scraper device similar to FIG. 1 but showing the blade in an open position relative to the handles for providing a rake head that can be drawn past a culture medium on an interior surface of the culture flask.

Referring to the drawings and particularly to FIGS. 1 and 2, there is illustrated a cell scraper device, generally designated 10, of the present invention. The cell scraper device 10 is adapted for use with a culture flask F in which microorganisms are grown on a culture medium on an interior surface of the culture flask F. The device 10 is particularly suited for collecting layers of cells grown inside the culture flask F although the device 10 is suitable for other applications as well.

The cell scraper device 10 basically includes a pair of elongated handles 12, a blade 14, and means 16 for pivotally joining the blade 14 to the handles 12. The handles 12 are for a user (not shown) to hold and to operate the device 10. The handles 12 together support the blade 14 for insertion into, manipulation within and removal from the culture flask F. The handles 12 and blade 14 are capable of reaching all interior surface areas of the culture flask F for collecting layers of cells growing on the culture medium on the interior surface of the culture flask F. The handles 12 and blade 14 are preferably, but not necessarily, made from a moldable plastic material, such as a plastic resin. The handles 12 and blade 14 can be molded separately or together by any suitable conventional technique, such as by injection molding of the plastic resin, depending upon the particular design of the means 16 for pivotally joining the blade 14 to the handles 12. The plastic resin can be a suitable polyolefin, such as polypropylene or polyethylene, though it may be some other suitable type of resin.

Referring now to FIGS. 1 to 5, each handle 12 of the device 10 has a substantially cylindrical configuration, though it need not be so limited, with a diameter which is substantially uniform along a longitudinal length of the handle 12 and with the longitudinal length being substantially greater than the diameter. The handles 12 are substantially identical and each has opposite ends 12A, 12B. The one end 12A of each handle 12 is generally free. The handle 12 defines a longitudinal axis A extending lengthwise between its opposite ends 12A, 12B. The longitudinal length of each handle 12 is greater than the height of the culture flask F and a longitudinal length of the blade 14. The handles 12 are spaced apart from and disposable along one another and, more specifically, in a substantially parallel relationship to one another. The handles 12 are movable in opposite directions along their longitudinal axes A. Thus, one of the handles 12 may be pushed forward or pulled backward while the other handle 12 is held in place or one of the handles 12 may be pushed forward or pulled backward while the other handle 12 is pulled backward or pushed forward to either laterally align the handles 12, as shown in FIG. 2, or to laterally offset the handles 12, as shown in FIG. 1.

The blade 14 of the device 10 is pivotally joined to the ends 12B of the handles 12 by the pivotal joining means 16. The blade 14 is movable between a closed position, as shown in FIG. 1, and an open position, as shown in FIG. 2, upon corresponding movement of the handles 12 in the opposite directions along the longitudinal axes A of the handles 12. The blade 14 is, preferably, movable between opposite closed positions and the open position. The blade 14 in one of the closed positions is disposed at a first acute angle B of a first size relative to the longitudinal axis A of each of the handles 12 and is disposed on a side of the handles 12, as shown in FIG. 1. The blade 14 in the other of the closed positions is also disposed at the first acute angle B of the first size relative to the longitudinal axis A of each of the handles 12 but is disposed on an opposite side of the handles 12 being a mirror image of that shown in FIG. 1. Thus, the blade 14 may be disposed on either side of the handles 12. The blade 14 in either closed position is positioned for insertion into and removal from the culture flask F through a top opening T thereof. The blade 14 in the open position is disposed in substantially transverse relation at a second angle C to each of the longitudinal axes A of the handles 12, as shown in FIG. 2, where the second angle C is of a second size substantially larger than the first size of the first angle B. The blade 14 in the open position thus provides a rake head that can be drawn past the culture medium on the interior surface of the culture flask F so as to collect and bring layers of cells growing on the culture medium to an area adjacent to the top opening T of the culture flask F for decanting the layers of cells from the culture flask F.

The blade 14 has a substantially flat rectangular configuration, though it need not be so limited. The blade 14 has opposite rear and front surfaces 14A, 14B, opposite end edges 14C and opposite side edges 14D. The blade 14 has a height extending between its opposite end edges 14C which may be slightly less or greater than or about the same as a length of the blade 14 extending between its opposite side edges 14d. One or more of scraping end and side edges 14C, 14D may be flat, as shown in FIG. 3, beveled, as shown in FIG. 4, or rounded, as shown in FIG. 5, or may have any other suitable configuration. The blade 14 is mounted or connected at its rear surface 14A to the ends 12B of the handles 12 at suitable locations spaced from one another and spaced inwardly from the opposite end edges 14C and from the opposite side edges 14D. In the illustrated examples, shown in FIGS. 1 to 5, each handle 12 is mounted to the blade 14 equidistantly between the opposite end edges 14C but closer to one of the opposite side edges 14D than to the other.

The pivotal joining means 16 of the device 10 includes a pair of spaced apart pivotal joints 18. As seen in FIGS. 1 to 5 and in greater detail in FIG. 6, in a preferred embodiment, each pivotal joint 18 is a ball joint type and includes a socket 20 and a ball 22 preferably made of a suitable flexible but resilient plastic material. The socket 20 can be in the form of a pair of spaced apart oppositelly facing halves 20A so that the ball 22 can be removably snap-fitted therebetween and thereby provided in a mated relationship within the socket 20 such that the respective handle 12 can pivot relative to the blade 14 in the opposite directions as represented by arrow D in FIG. 6. In the illustrated embodiment, the socket 20 is formed on the rear side 14A of the blade 14 and the ball 22 is formed on the end 12B of the handle 12, although these locations of the socket 20 and ball 22 could be reversed. The sockets 20 of the pivotal joints 18 are spaced apart from one another between the opposite side edges 14D of the blade 14 such that one socket 20 is closer to one of the side edges 14d, while the other socket 20 is closer to the other of the side edges 14D. The sockets 20 are both located substantially equidistantly between the opposite end edges 14C of the blade 14. Thus, the blade 14 is movable between one or the other of the closed positions and the open position upon corresponding movement of the handles 12 in opposite directions along the longitudinal axes A of the handles 12.

Referring to FIG. 7, in an alternative embodiment, the pivotal joining means 16 can be a pair of living hinge joints 24 pivotally joining the blade 14 to the pair of adjacent ones 12B of the opposite ends 12A, 12B of the handles 16. The pivotal living hinge joints 24 permit pivotal movement of the handles 12 relative to the blade 14 in the opposite directions as represented by arrow E in FIG. 7 upon the handles 12 being moved longitudinally relative to one another.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A cell scraper device, comprising:

(a) a pair of elongated handles for enabling a user to hold and to operate said device, each of said handles having a pair of opposite ends and defining a longitudinal axis extending between said opposite ends, said handles being spaced apart from and disposable along one another and movable in opposite directions along said longitudinal axes (b) a blade; and (c) means for pivotally joining said blade to a pair of adjacent ones of said ends of said handles such that said blade is pivotally movable between a closed position and an open position upon corresponding movement of said handles in said opposite directions along said longitudinal axes of said handles, said blade in said closed position being disposed at an angle of a first size relative to said longitudinal axis of each of said handles along a side of said handles at said pair of adjacent ones of said ends thereof such that said blade and handles are positioned for insertion into and removal from a culture flask through a top opening thereof, said blade in said open position being disposed at another angle of a second side relative to said longitudinal axis of each of said handles which is larger than said angle of said first size such that said blade provides a rake head that can be drawn past a culture medium on an interior surface of the culture flask so as to collect and bring layers of cells growing on the culture medium to an area adjacent to the top opening of the culture flask for decanting the layers of cells from the culture flask.

2. The device of claim 1 wherein said handles are substantially identical.

3. The device of claim 1 wherein each said handle has a longitudinal length greater than a longitudinal length of said blade.

4. The device of claim 1 wherein said blade has a substantially flat rectangular configuration.

5. The device of claim 1 wherein said blade has a bottom edge which is flat.

6. The device of claim 1 wherein said blade has a bottom edge which is beveled.

7. The device of claim 1 wherein said blade has a bottom edge which is rounded.

8. The device of claim 1 wherein said means for pivotally joining said blade to said handles is a pair of spaced apart pivotal ball joints each pivotally connecting said blade to one of said adjacent ends of said pair thereof of said handles.

9. The device of claim 8 wherein each of pivotal ball joints includes:

a socket mounted to one of said blade and said one end of said pair thereof of said handles; and a ball mounted to the other of said blade and said one end of said pair thereof of said handles, said balls of said pivotal ball joints being rotatably interfitted with said sockets thereof.

10. The device of claim 1 wherein said means for pivotally joining said blade to said handles is a pair of living hinge joints each pivotally connecting said blade to one of said adjacent ends of said pair thereof of said handles.

11. A cell scraper device, comprising:

(a) a pair of elongated handles for enabling a user to hold and to operate said device, each of said handles having a pair of opposite ends and defining a longitudinal axis extending between said opposite ends, said handles being spaced apart from and disposable along one another and movable in opposite directions along said longitudinal axes;

(b) a blade;

(c) means for pivotally joining said blade to a pair of adjacent ones of said ends of said handles such that said blade is pivotally movable between opposite closed positions and an open position upon corresponding movement of said handles in said opposite directions along said longitudinal axes of said handles, said blade in said opposite closed positions being disposed at acute angles relative to said longitudinal axes of said handles and disposed on either side of said handles at said pair of adjacent ones of said ends thereof such that said blade and handles are positioned for insertion into and removal from a culture flask through a top opening thereof, said blade in said open position being disposed in a substantially transverse relationship to said longitudinal axes of said handles such that said blade provides a rake head that can be drawn past a culture medium on an interior surface of the culture flask so as to collect and bring layers of cells growing on the culture medium to an area adjacent to the top opening of the culture flask for decanting the layers of cells from the culture flask.

12. The device of claim 11 wherein said handles are substantially identical.

13. The device of claim 11 wherein each said handle has a longitudinal length greater than a longitudinal length of said blade.

14. The device of claim 11 wherein said blade has a substantially flat rectangular configuration.

15. The device of claim 11 wherein said blade has a bottom edge which is flat.

16. The device of claim 11 wherein said blade has a bottom edge which is beveled.

17. The device of claim 11 wherein said blade has a bottom edge which is rounded.

18. The device of claim 11 wherein said means for pivotally joining said blade to said handles is a pair of spaced apart pivotal ball joints each pivotally connecting said blade to one of said adjacent ends of said pair thereof of said handles.

19. The device of claim 18 wherein each of pivotal ball joints includes:

a socket mounted to one of said blade and said one end of said pair thereof of said handles; and a ball mounted to the other of said blade and said one end of said pair thereof of said handles, said balls of said pivotal ball joints being rotatably interfitted with said sockets thereof.

20. The device of claim 11 wherein said means for pivotally joining said blade to said handles is a pair of living hinge joints each pivotally connecting said blade to one of said adjacent ends of said pair thereof of said handles.

* * * * *